US011291818B2

(12) United States Patent
Admati et al.

(10) Patent No.: US 11,291,818 B2
(45) Date of Patent: Apr. 5, 2022

(54) MICRONEEDLE STRUCTURE FOR INTRADERMAL INJECTION

(71) Applicant: NanoPass Technologies Ltd., Ness Ziona (IL)

(72) Inventors: Gal Admati, Kibbutz Dorot (IL); Yoav Hamisha, Mazkeret Batiya (IL); Yotam Levin, Ness Ziona (IL)

(73) Assignee: NANOPASS TECHNOLOGIES LTD., Ness Ziona (IL)

( * ) Notice: Subject to any disclaimer, the term of this patent is extended or adjusted under 35 U.S.C. 154(b) by 85 days.

(21) Appl. No.: 16/837,080

(22) Filed: Apr. 1, 2020

(65) Prior Publication Data

US 2021/0308439 A1 Oct. 7, 2021

(51) Int. Cl.
*A61M 37/00* (2006.01)

(52) U.S. Cl.
CPC ... *A61M 37/0015* (2013.01); *A61M 2037/003* (2013.01); *A61M 2037/0023* (2013.01); *A61M 2037/0038* (2013.01); *A61M 2037/0053* (2013.01)

(58) Field of Classification Search
CPC ...... A61M 37/0015; A61M 2037/0038; A61M 2037/0053; A61M 2037/003; A61M 2037/0023
See application file for complete search history.

(56) References Cited

U.S. PATENT DOCUMENTS

| 2006/0015061 A1* | 1/2006 | Kuo | A61B 17/205 604/47 |
| 2017/0266394 A1* | 9/2017 | Admati | A61M 5/3213 |

* cited by examiner

*Primary Examiner* — Amber R Stiles
(74) *Attorney, Agent, or Firm* — Mark M. Friedman

(57) ABSTRACT

A microneedle for intradermal injection or diagnostics, constructed as a protrusion above a substrate and whose shape is defined by a pair of vertical side surfaces, configured to be symmetrical about a vertical plane of symmetry and to meet along a vertical leading edge, and by an inclined surface, intersecting the side surfaces, the microneedle also including a vertical bore, located centrally between the two side surfaces and substantially near the leading edge,
wherein each of the side surfaces is divided, sequentially along the front-to-back direction, into at least two contiguous planar segments, forming pairs of corresponding segments along the respective side surfaces; each pair of corresponding segments mutually form an acute angle, the angle being between 40 and 70 degrees for the pair of segments adjacent the leading edge and less than 35 degrees for the pair of segments farthest from the leading edge
and wherein the leading edge is formed so that its profile includes an arc, joined to the side surfaces.

10 Claims, 3 Drawing Sheets

| Model | Curvature radius [um] | Hole distance from curvature [um] | Minimal wall thickness (driven) [um] |
|---|---|---|---|
| PR_1011 (original) | 0 | 112 | 29.83 |
| PR_1016 | 5 | 112 | 32.49 |
| PR_1017 | 15 | 112 | 35.78 |
| PR_1018 | 25 | 112 | 36.02 |
| PR_1019 | 35 | 112 | 36.26 |
| PR_1020 | 5 | 108 | 30.34 |
| PR_1021 | 15 | 100 | 30.67 |
| PR_1022 | 25 | 90 | 29.92 |
| PR_1023 | 35 | 85 | 31.86 |
| PR_1024 | 0 | 170 | 37.37 |

MICRONEEDLE STRUCTURE FOR INTRADERMAL INJECTION

TECHNICAL FIELD

The invention is directed to intradermal injection devices and, in particular, to a microneedles array device for oblique skin penetration.

BACKGROUND OF THE INVENTION

Microneedles, as used herein, are relatively short needles with a length generally below 1 mm and lateral dimensions typically a few hundreds of microns at most. They are usually arranged in an array and serve to inject a fluid into a skin tissue or to pump fluids therefrom for diagnostics. Microneedles can be manufactured using various manufacturing techniques ranging from use of steel cannulas, polymers or silicon, and can be made in a variety of production processes including micro-injection molding, hot embossing, wire/laser cutting, radiation and MEMS, among other methods. One particularly advantageous microneedle structure suitable for use in implementing the present invention is described in US patent application 2009/0247953. Such a structure is depicted, for example, in FIG. 1 and includes an array of microneedles 1 protruding from a substrate 10; each microneedle is formed with two vertical side surfaces 6, two vertical edge surfaces that meet along a vertical edge 3 and an inclined surface 7; a vertical bore 2 extends through the entire length of the microneedle. The microneedles are designed so that they may penetrate the skin surface at an oblique angle thereto.

U.S. Pat. No. 7,998,119—incorporated herein by reference—discloses an adapter that includes an array of microneedles, designed to be fluidly connected with a device for delivering drugs or other liquids into the skin or another biological membrane, or for sampling fluids therefrom, such a device including, but not limited to, a syringe, a dosed drug delivery device, a drug delivery patch and an infusion device. Such an adapter, for example, is shown, as a sectional view, in FIGS. 1B and 1C. It includes an array of microneedle 12 on a substrate 10 (which is attached to a non-referenced device coupling member). In FIG. 1B the adapter is shown in relation to the surface of a skin 14 as it would at the beginning of operation. It would then be pressed against the skin, depressing part of it, and be slid to the left (as indicated by the horizontal arrow), thereby letting the microneedles pierce and penetrate the skin—in effect obliquely—at the area of transition toward an undepressed part thereof. The adapter, with the attached device, would then be turned (as indicated by the circular arrow) into a position depicted in FIG. 1C, where it will be ready for the respective injection or fluid sampling operation.

Several operational characteristics are desired or required of microneedles, including for example—
(a) Ease of skin penetration, with minimum pain to the patient
(b) Large ratio of injection depth to penetration depth (which is equivalent to the ratio of bore length to needle height)
(c) Small impedance (or resistance) to the flow of fluid through the bore, so as to maximize flow rate at a given driving pressure
(d) Minimal leakage of injected fluid to outside the skin
(e) Mechanical robustness, i.e. minimal probability of needle breakage during operation Microneedles of prior art do not generally provide optimal values of all the desired or required operational characteristics, such as listed above.

SUMMARY OF THE INVENTION

There is disclosed a microneedle and an array of microneedles for delivery of substances into viable human tissue, such as, but not limited to, intradermal compartments and ocular- and gynecological tissues. Such a microneedle or array of microneedles may also be used for diagnostics of the tissue. A microneedle according to the invention is constructed so as to simultaneously provide a plurality of satisfactory operational characteristics.

Specifically there is disclosed a microneedle for intradermal injection or diagnostics, constructed as a protrusion above a substrate and whose shape is defined by a pair of vertical side surfaces, configured to be symmetrical about a vertical plane of symmetry and to meet along a vertical leading edge, and by an inclined surface, intersecting the side surfaces, the microneedle also including a vertical bore, located centrally between the two side surfaces and substantially near the leading edge, wherein each of the side surfaces is divided, sequentially along the front-to-back direction, into at least two contiguous planar segments, forming pairs of corresponding segments along the respective side surfaces; each pair of corresponding segments mutually form an acute angle, the angle being between 40 and 70 degrees for the pair of segments adjacent the leading edge and less than 35 degrees for the pair of segments farthest from the leading edge and wherein the leading edge is formed so that its profile includes an arc, joined to the side surfaces.

In some embodiments the arc is part of a circle and its radius is between 20 and 50 microns.

In some embodiments the shortest distance, along the plane of symmetry, between the leading edge and the bore is less than 120 microns.

In some embodiments the number of the segments in each of the side surfaces is at least three and the angle is greatest for the pair of segments adjacent the leading edge and successively diminishes in value for sequentially contiguous pairs. In some of these embodiments the joint between any two adjoining ones of the segments on any of the side surfaces is formed so that its profile includes an arc. In some embodiments in which the number of segments of each side surface is three, the value of the angle for the pair of segments next adjacent to the pair of segments adjacent the leading edge is between 15 and 35 degrees and for the next adjacent pair of segments—between 0 and 20 degrees.

In some embodiments the shortest distance between any one of the segments and the bore does not exceed 35 microns.

In some embodiments the cross-sectional shape of the bore has a front-to-back dimension greater than the width dimension. In some of them the cross-sectional shape is an oval or an asymmetrical oval, defined by a front radius and a rear radius, the front radius being larger than the rear radius.

BRIEF DESCRIPTION OF THE DRAWINGS

The invention is herein described, by way of example only, with reference to the accompanying drawings, wherein:

FIG. 3A is a front view, FIG. 3B is a top view, FIG. 3C is a front sectional view, FIG. 3D is a sectional side view; FIGS. 3E and 3F show enlarged details in FIG. 3B at different scales.

FIG. 4A is a chart showing the breaking force for several models and FIG. 4B is a table, listing certain measures of several models.

DETAILED DESCRIPTION OF THE PREFERRED EMBODIMENTS

Figure 1A:
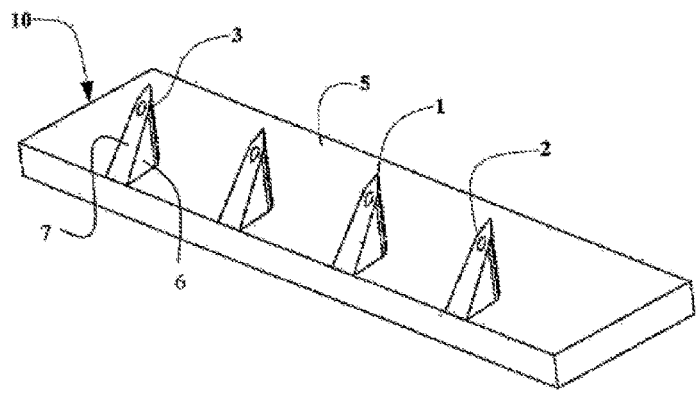
FIG. 1A is an isometric view of a microneedle array of prior art, to which a design according to an embodiment of the present invention is applicable.
Figure 1B:
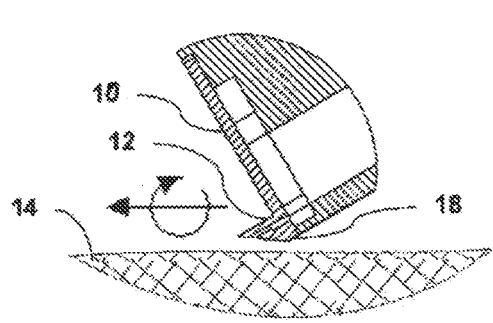
FIGS. 1B and 1C are sectional views of a microneedle array in an example configuration, illustrating a mode of its use.
Figure 1C:
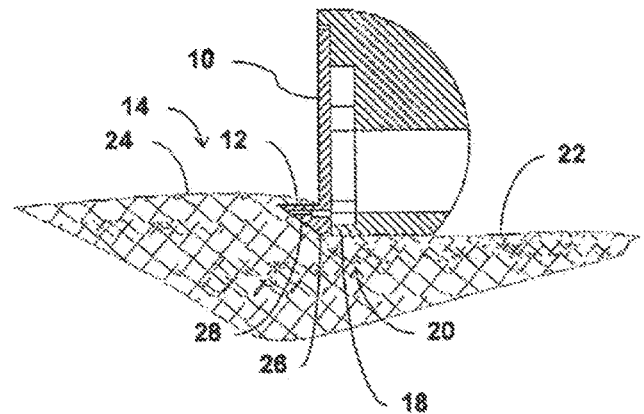
Figure 2:
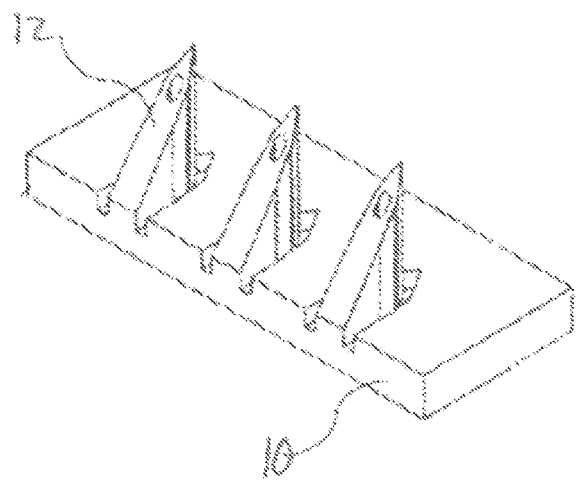
FIG. 2 is an isometric view of a microneedle array according to an embodiment of the present invention.

An embodiment of the invention will now be described, by way of example, with reference to FIGS. 2 and 3A-3F. FIG. 2 is an isometric view of a microneedle array for intradermal or ocular injection, which is generally similar to that disclosed in international application WO 2017/072770A1 but differs therefrom in several significant details, to be described below. The array is seen to consist of a row of microneedles 12 protruding from a substrate 10. The overall structure of the array and its methods of fabrication are similar to those described above with respect to FIG. 1. The number of microneedles in the row may be any, including one.

The structure of the array of FIG. 2 and of each microneedle, according to the invention, is discussed below in relation to the aforementioned operational requirements and is followed by a description, in greater detail, of the illustrated example embodiment.

It is noted that in all the present drawings the array and the microneedles are depicted in an orientation wherein the large surfaces of the substrate are parallel to a horizontal plane and the microneedles protrude upwards (i.e. their side surfaces are vertical). In operation the array would generally assume different orientations, as illustrated for example in FIGS. 1B and 1C (where the substrate 16 is shown inclined or in a vertical orientation, respectively). However, for clarity and consistency throughout the present disclosure, all references to directions, dimensions, etc. will assume the orientation as depicted in FIGS. 2 and 3A-3F. In particular, dimensions across the page in FIGS. 3A, 3B and 30 will be referred to as width dimensions, dimensions lengthwise the page in FIGS. 3A, 3C and 3D will be referred to as height dimensions and dimensions lengthwise FIG. 3B, as well as across FIG. 3D, will be referred to as front-to-back dimensions, where front corresponds to the up direction in FIG. 3B. The front direction is also referred to as the leading direction (in view of FIG. 1B). All the dimension values in the drawings are in microns and are non-limiting, but serve as typical examples; ranges of values in various embodiments are given where appropriate, but should not be construed as limiting.

Generally a microneedle, according to embodiments of the invention, is constructed as a protrusion (above a substrate) whose shape is defined by a pair of vertical side surfaces, configured to meet along a vertical common edge (to be referred to as the leading edge), and by an inclined planar surface (to be referred to as the inclined surface), delineated by the side surfaces. The intersection of the inclined surface with the leading edge forms a pointed apex. The microneedle also includes a vertical bore, located, generally centrally, between the two side surfaces and substantially near the leading edge. The bore in these embodiments has a cross-sectional shape that is symmetrical about a front-to-back [or longitudinal] vertical plane, which plane also forms a plane of symmetry with respect to the side surfaces. The height of the needle is determined primarily by the required depth of penetration, which is dictated by anatomical and clinical requirements. Embodiments described herein, by way of example, address the needs of injection into the epidermis, whose thickness is typically between 500 and 1000 microns. Accordingly the height of each microneedle in the illustrated embodiment is typically 600 microns, but may range between 500 and 900 microns.

Several other requirements apply to the structure and shape of each microneedle, in order to provide the above-listed desired operational characteristics, as follows:

(a) The width of the microneedle (i.e. the distance between the side surfaces) should be as small as possible, in order to minimize pain and facilitate penetration.

(b) The angle of the inclined surface should be chosen to provide the desired degree of overall sharpness of the microneedle, to, again, facilitate penetration; this determines also the front-to-back dimension of the microneedle (as measured in a horizontal plane), which, again, should be as small as possible, in order to minimize pain.

(c) The cross-sectional area of the microneedle, at any level, should be large enough to assure its robustness, i.e. its ability to withstand various forces that may act on it during operation.

(d) The cross-sectional area of the bore should be large enough to present relatively low impedance to the flow of liquid during the process of injection and thus allow the required flow rate.

(e) The leading edge should be sharp enough so as to enable relatively easy penetration of skin surface during the usually oblique insertion process.

(f) The distance between the bore and the leading edge should be small, so that its opening (which is near the apex of the needle) will reach maximum possible depth of injection, relative to depth of penetration (which mainly depends on the needle height); this also minimizes the probability of leakage of injected fluid.

These requirements are, in part, mutually conflicting; for example, small width and sharpness must be balanced against robustness. Microneedles with conventional forms and structure do not optimally meet all of the requirements.

In embodiments of the invention, the shape and dimensions of each microneedle, as defined over any horizontal cross-sectional plane (i.e. as seen in a top view), are determined so as to optimally meet the structural requirements enumerated above. In particular, the part of the microneedle near the leading edge and including the bore is formed on the basis of the following principles:

(1) The thickness of the wall surrounding the bore (i.e. the shortest distance between the bore and the external surface of the microneedle) may vary with the azimuth, but at no point is it less than a minimal value, required to maintain mechanical robustness.

(2) The leading edge is formed as a circular arc with a non-zero radius, tangent to the converging side surfaces; this enables shortening the distance between the leading edge and the bore (per requirement above), as well as the overall front-to-back dimension of the microneedle, without detracting from its robustness; furthermore the strength of the sharp apex (the top corner of the leading edge) is thereby enhanced.

(3) The cross-sectional shape of the bore is elongated along the front-to-back axis, so as to increase its area while keeping the width of the needle to a minimum.

A further principle, concerning the overall shape of the microneedle, is that each of the side surfaces is divided, sequentially along the front-to-back direction, into at least two contiguous planar segments; a first segment begins with the leading edge and forms an acute angle with the corresponding first segment of the other side surface; each successive segment is oriented with the corresponding segment of the other side surface at an acute angle that is smaller than that of the previous segment, i.e. the segments become successively closer to being parallel. In some embodiments the nearest distance between a second one of the segments and the bore is essentially equal to the minimal required value of the bore wall thickness.

In some embodiments, the cross-sectional shape of the bore has a front-to-back dimension greater than the width dimension. In various configurations the cross-sectional shape is an oval. In some configurations the cross-sectional shape is an asymmetrical oval, defined by a first radius, at the back end, and a second radius, at the front end, where the second radius is smaller than the first radius. This asymmetric geometry facilitates maintaining the required minimum wall thickness surrounding the bore while at the same time providing enhanced overall cross-sectional area, for lower fluid flow impedance.

An example embodiment of the invention will now be described in greater detail, Specific values of dimensions given herein are typical values, obtained through comparative experiments as satisfying operational requirements, such as listed in the Background section above, for some applications. For other applications and with different weights given to the operational requirements, other values may optimally apply.

Figure 3A:
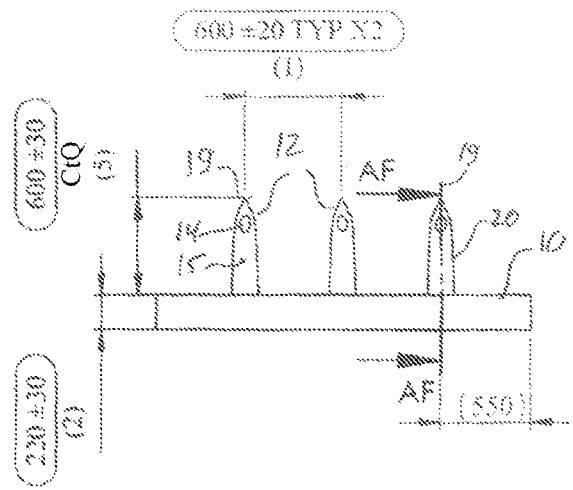
FIGS. 3A-3F are various planar projections of the array of FIG. 2, showing novel structural details. In particular.
Figure 3D:
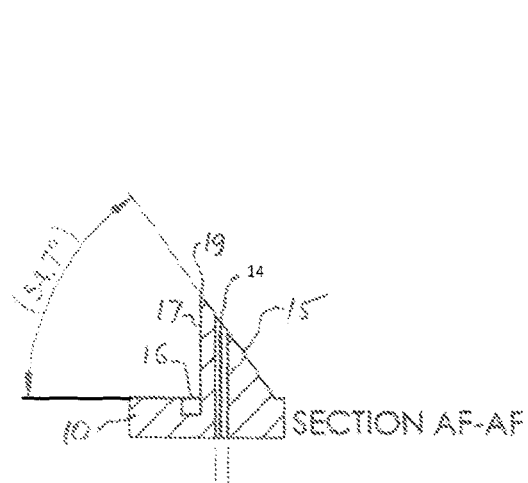
Figure 3B:
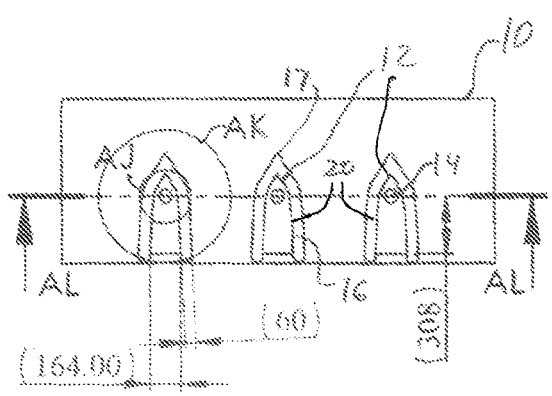

FIGS. 3A and 3B are a front- and top view, respectively, of the microneedle array. In FIG. 3B vertical bores 14 are visible head on; their top openings are visible in FIG. 3A, since they appear on inclined surface 15. A sectional elevation view (AL-AL in FIG. 3B) in a plane that includes bores 14 is shown in FIG. 3C. Likewise, a front-to-back sectional view (AF-AF in FIG. 3A) in a vertical plane of symmetry 19, is shown in FIG. 3D. Visible therein are the bores 14 extending down through the microneedle and into the substrate 10, which are to serve for conducting fluid into, or out of, a tissue. Also visible are grooves 16, etched into the substrate and surrounding the bases of the microneedles 12, which are dictated by the fabrication process, but are not a necessary feature of a microneedle according to the invention.

The vertical side-surfaces 20 of each microneedle (whose shape will be further described below) converge at a common vertical leading edge 17, which is formed with some rounding; that is, its profile (i.e. cross-sectional shape) includes an arc 18, joined tangentially to the side-surfaces 20. FIG. 3F shows an enlarged top view of the leading part of the microneedle. As seen therein, the bore 14 is located centrally between the side surfaces 20. Its cross-sectional shape is slightly elongated in the front-to-back direction (as further explained below) and defined by two semi-circles—one toward the front and one toward the back, with radii of 30 and 31 microns, respectively. The arc 18 of the edge 17 is, in this embodiment, a part of a circle and its radius is seen to be 35 microns, while the convergence angle of the side surfaces 26 is 65°. The corresponding distance, along the plane of symmetry 19, between the arc 18 of edge 17 and the focus of the front semi-circle of the bore 14 is 85 microns. Accordingly, the nearest distance, along the plane of symmetry 19, between arc 18, (i.e., edge 17) and the bore is 85−30=55 microns. Although tests have shown that a value of 35 microns for the radius of the arc represent an optimal compromise, this value may range, in various embodiments, between 5 and 50 microns, with a corresponding variation in the distance value.

Surface 15 of each microneedle is an inclined plane; the angle of inclination is typically 54.7° from the horizontal, but may be between 50 and 60 degrees, or, in some embodiments, between 40 and 65 degrees. The intersection of inclined surface 15 with leading edge 17 forms a sharp corner at the apex 19 of the microneedle. The height of each needle, from a top surface of substrate 10 to the apex 19, is 600 microns but may generally be between 100 and 1000 microns, and depending upon the intended application, is typically between 400 and 800 microns for delivery of medicaments, and between 100 and 400 microns for delivery of cosmetic compositions.

Figure 3E:
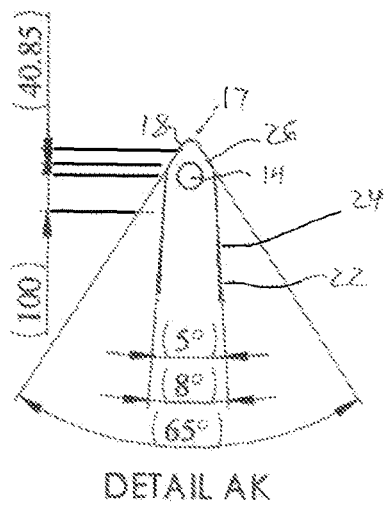
Figure 3C:
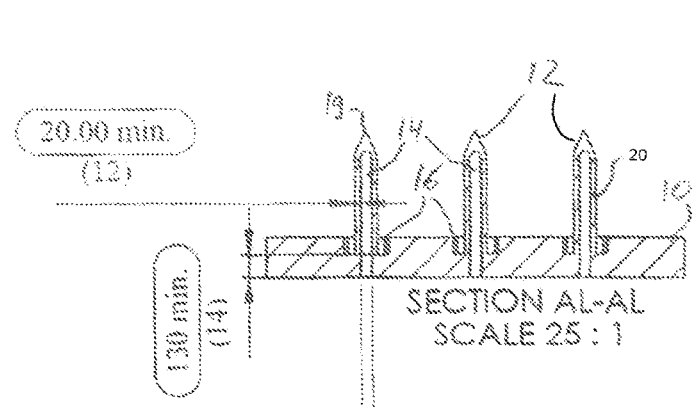
Figure 3F:
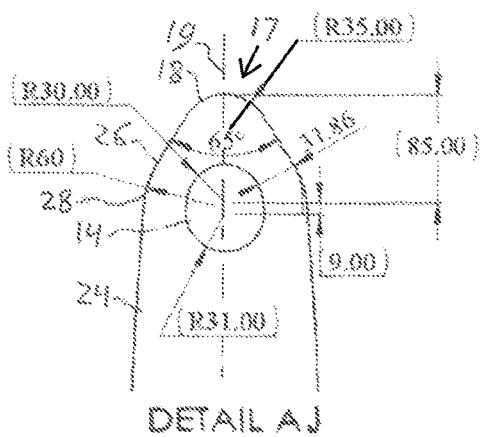

Vertical side surfaces 20 are visible as profiles in the top view of FIG. 3B and, enlarged, in the detail view of FIG. 3E as well as, further enlarged, in the detail view of FIG. 3F. The horizontal distance between the two side surfaces 20 of each microneedle, at any point along a front-to-back axis, determines the width (or thickness) of the microneedle at that point. Generally, the width is greatest near the back of the microneedle (i.e. where its height is small); typically it is 164 microns, but may range between 100 and 175 microns and, in some embodiments, between 60 and 200 microns. The width diminishes gradually (as further explained below) toward the leading edge 17, where its value becomes close to twice the radius of its arc. One of the structural requirements listed above (as item 'a') is that the width of the microneedle be as small as possible, while another requirement (item 'c' in that list) is that the structure be robust. The second requirement conflicts with the first one, as it implies greater width. The generally diminishing width of the microneedle in the described embodiment of the invention may optimally resolve this conflict, in that the width is large near the back, where the height (between the substrate and the inclined surface) is small, and, conversely, small nearer the front of the microneedle, where the height is greater. The effect of this feature is, on the one hand, greater average width near the base of the microneedle, where any externally induced bending moment would be greatest, thus retaining robustness, and, on the other hand, smaller width near the tip of the microneedle, where the depth of penetration into the skin is greatest, thus easing penetration and diminishing pain.

The width of bore 14 has been chosen to be about 60 microns, but may range between 50 and 80 or, in some embodiments, between 40 and 120 microns. The bore's dimension in the front-to-back direction is somewhat longer—by about 10 microns in the example embodiment or, in other embodiments, considerably more—making its cross-sectional shape to be oval, rather than circular, and thus having a greater area-to-width ratio. It is noted that these dimensions result in reasonably low impedance to liquid flow (satisfying item 'd' in the aforementioned list of requirements), while allowing a relatively small overall width value for the microneedle near the bore (satisfying also item 'a' in that list). The minimal required thickness of the wall formed between the bore 14 and a side surface 20, as dictated, for example, by structural considerations, is typically 20 microns, though in other embodiments it may also range down to about 10 microns. Thus the overall minimum practical width (i.e. distance between the two side surfaces) near the bore is typically 60+2*20=100 microns (though in some embodiments it may be as low as 40+2*10=60 microns). It is noted that, in certain embodiments, the profile of each side surface is designed so that its closest distance from the bore is essentially equal to that minimal required bore wall thickness. More generally, and as a novel feature of embodiments of the invention, this closest distance does not exceed 25 microns.

As noted above, the cross-sectional shape of the bore 14 in example embodiments is an oval, wherein the term oval is to be understood as any elongated shape with at least two curved segments and may include an ellipse. In some embodiments the oval may be defined by two circular segments—a front segment (nearer the leading edge) and a rear segment (farther from the leading edge)—joined, for example, by straight tangent, or otherwise intersecting, lines. In some embodiments such an oval is asymmetric (e.g. drop shaped), wherein the two circular segments have mutually different radii and the tangent lines are non-parallel. Preferably, the front radius (i.e., radius of the front segment) is larger than the rear radius (i.e., radius of the rear segment); this conforms with the adjacent parts of the side surfaces 20 being convergent toward the front, i.e. toward the leading edge 17 (as described above). In the illustrated embodiment the shape is an asymmetric oval, with the respective radii being 30 and 31 microns and the distance between their foci being 9 microns. Clearly, also other values may be used. The advantage of an asymmetric oval is that it enables increasing the cross-sectional area of the bore by increasing also its width (in addition to the aforementioned increase in length) at a point further to the back, where also the overall width of the microneedle is greater, while maintaining the required wall thickness (e.g. 20 microns in the illustrated embodiment) between the bore and each side surface.

In the exemplary embodiment, each side surface 20 consists—sequentially in the back-to-front direction—of three vertical planar segments 22, 24, 26, mutually joined, edge to edge, at obtuse angles, as can be seen in FIGS. 3E and 3F. Each such segment is inclined with respect to the front-to-back axis at a successively increasing angle; looking at the sequence conversely, the angle of inclination diminishes along the front-to-back direction, from a large value for the leading segment 26 to a small value for the trailing segment 22. The joint between any two adjoining planar segments form an obtuse vertical edge, which may be rounded, so that its profile (i.e. cross-sectional shape) include an arc. Thus, in the exemplary embodiment, as can be seen in FIG. 3F, the profile of the joint between each leading segment 26 and the next segment 24 includes an arc 28, whose radius is typically 60 microns.

Generally, the number of segments on the two side surfaces is equal, e.g. three as in the illustrated embodiment, and thus corresponding segments thereof may form generally symmetric pairs, whereby the angles of inclination of each pair with respect to the plane of symmetry combine to form a common acute angle, which is clearly denoted in FIG. 3E. Clearly, the value of the total angle of each pair of segments successively diminishes—from a large value for the pair at the front, i.e. adjacent the leading edge, to a small value for the pair at the back. Typical values of these total angles for the illustrated example embodiment are given in FIG. 3E and are explained in what follows. It is noted that, with these characteristics, the segments together impart to each side surface a particular convex profile in keeping with the general characteristic of back-to-front diminishing width, discussed hereabove.

The backmost pair of segments 22 are shown to mutually converge at (i.e. form an angle of) typically 5°; the value of the angle may range between 15° and zero (i.e. parallel). The segments begin with a distance between them (i.e. maximum width of needle, as described above) of typically 164 microns and typically extend approximately halfway toward the front of the microneedle. The middle pair of segments 24 mutually converge at (i.e. form an angle of) typically 15°; the value of the angle may range between 15 and 35 degrees. These second pair of segments typically extends to approximately near the leading part of the bore. It is noted that the distance between the side surfaces at that point is typically about 100 microns (though in some configurations it may be as low as 60 microns)—which, as explained above, is the minimal practical distance that satisfies the stated requirements. It is further noted that the combined effects of the convergence of segments 22 and 24 causes the width of the microneedle to gradually diminish from the given value of 164 microns to the given value of 100 microns at the bore. The advantage of using two planes with successively increasing angle of convergence, over using a single plane that reaches similar width near the bore, is that this enables specifying a smaller width at the back of the needle for any given average width (dictated by the robustness requirement). Clearly, in other configurations, other values of width and commensurately other values of convergence angles are possible. Also, the same part of the side walls may be similarly divided into more than two segments and any of these may, in some configurations, also be non-planar.

Finally, the leading pair of segments 26 meet each other along the leading edge 17. Their combined angle of convergence is roughly 65° in the example illustrated here (FIG. 3E), but may generally range between 50 and 65 degrees, in some embodiments—between 40 and 70 degrees. This value represents a compromise between, on the one hand, the requirement of short distance between the bore and the leading edge 17 (item 'f' of the aforementioned list) as well as the requirement of small overall front-to-back dimension, as dictated by the angle of the inclined surface (item 'b' of the aforementioned list) and, on the other hand, the requirement of a sharp leading edge (item 'e' of the list). Clearly, in other configurations, other values of angle may be chosen—representing different weights given to the requirements.

The effective distance of the leading edge from the bore is further reduced by shaping the edge profile as a circular (or optionally elliptical) arc 18 (FIG. 3F), as described above. The radius of that arc is directly related to its distance from the bore 14; its value is typically between 25 and 35 microns, but may range, in some embodiments, between 5 and 50 microns. For the typical values of convergence angle and of radius of the edge profile, stated above, the nearest distance, along the plane of symmetry, between the bore and the arc 18, is typically between 55 and 60 microns, but may, in some embodiments, be up to 120 microns.

Experimental Data

The above typical values of the radius of the edge profile and the distance of the edge from the bore, which are considered a novel feature of the invention, have been obtained by systematic and careful mechanical strength testing of a number of microneedle array models, similar to those described herein but constructed with different values of certain dimensions. The object of the tests was to determine dimensional values that allow attaining maximal mechanical strength, as well as injection depth while keeping to the desired ease of penetration and minimal leakage of fluid.

Figures 4A, 4B:
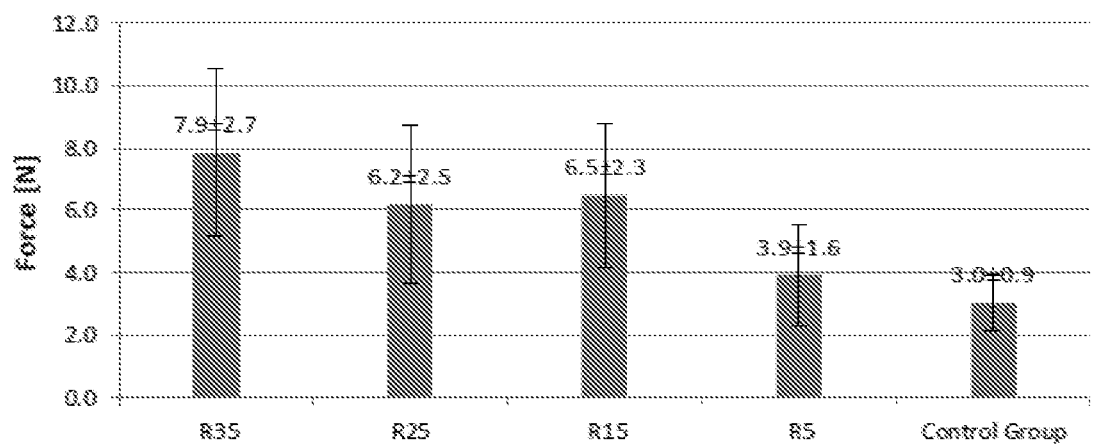
FIGS. 4A and 4B show data related to experimental evaluation of model embodiments of the invention.

During a first phase of testing, models with various values of the radius of curvature of the leading edge 17 (i.e., radius of arc 18 of the edge profile), but otherwise similar, were tested for mechanical strength. FIG. 4A is a bar diagram of the results, in which the bars are denoted by the value of the radius, in microns, and the ordinate values are those of the force, in newtons, required to break a needle. It may be seen that the breaking force (and consequently also the microneedle strength) largely decreases with decreasing radius and that a radius between 15 and 35 microns is significantly superior in this regard.

During a second phase, tested models differed from each other in both the radii of edge curvature and the distance between the leading edge and the nearest center of curvature of the bore (hole). The values of their respective parameter values (as well as the derived minimal wall thickness between the bore and the side surfaces) are listed in a table shown in FIG. 4B. The results of this phase corroborated those of the first phase, namely the direct relation between strength and radius of curvature. Additionally the results indicated that the strength was not significantly related to the edge-to-bore distance. The latter observation allows choosing a relatively low value for this distance—notably 85 to 90 microns from edge to bore center—without significantly detracting from the mechanical strength. Using the corresponding low values of 55 to 60 microns for the net edge-to-bore distance has the advantage of achieving maximum possible injection depth and thereby also minimizing leakage.

It is noted that the rounding of the leading edge, as described above, has a further advantage, namely greater local mechanical strength, by avoiding the brittleness of a too sharp corner edge and a too sharp apex. It is further noted that the effective sharpness of the microneedle, i.e. its penetration ability, is not appreciably reduced by this rounding and is not less than that of a conventional steel injection needle.

It will be appreciated that the above descriptions are intended only to serve as examples and that many other embodiments are possible within the scope of the present invention as defined in the appended claims.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

The invention claimed is:

1. A microneedle for intradermal injection or diagnostics, comprising a protrusion above a substrate and whose shape is defined by—
—a pair of vertical side surfaces, configured to be symmetrical about a vertical plane of symmetry and to meet along a vertical leading edge, and by—
—inclined surface, intersecting the side surfaces,
the microneedle also comprising a vertical bore, located centrally between the two side surfaces and substantially near said leading edge,
wherein each of said side surfaces is divided, sequentially along a front-to-back direction, into at least two contiguous planar segments, forming pairs of corresponding segments along the respective side surfaces; each pair of corresponding segments annually form an acute angle, said angle being between 40 and 70 degrees for the pair of segments adjacent the leading edge and less than 35 degrees for the pair of segments farthest from the leading edge and
wherein said leading edge is formed so that its profile includes an arc, joined to said side surfaces.

2. The microneedle of claim wherein said arc is part of a circle and its radius is between 20 and 50 microns.

3. The microneedle of claim 1, wherein a shortest distance, along said plane of symmetry, between said leading edge and said bore is less than 120 microns.

4. The microneedle of claim. 1, wherein a number of said segments in each of the side surfaces is at least three and said angle is greatest for the pair of segments adjacent the leading edge and successively diminishes in value for sequentially contiguous pairs.

5. The microneedle of claim 4, wherein any two adjoining ones of said segments on any of the side surfaces formed a vertical joint whose profile include an arc.

6. The microneedle of claim 4, wherein said angle for the pair of segments next adjacent to the pair of segments adjacent the leading edge is between 15 and 35 degrees and for the pair of segments farthest from the leading edge—is between 0 and 20 degrees.

7. The microneedle of claim 4, wherein the a shortest distance between any one of said segments and said bore does not exceed 35 microns.

8. The microneedle of claim 1, wherein a cross-sectional shape of the bore has a front-to-back dimension greater than the width dimension.

9. The microneedle of claim 8, wherein said cross-sectional shape is an oval.

10. The microneedle of claim. 9, wherein said cross-sectional shapeis an asymmetrical oval, defined by a front radius and a rear radius, the front radius being larger than the rear radius.

* * * * *